United States Patent [19]

Frimberger

[11] Patent Number: 4,649,916

[45] Date of Patent: Mar. 17, 1987

[54] STIFFENING PROBE AND TENSIONING DEVICE THEREFOR

[75] Inventor: Eckart Frimberger, Munich, Fed. Rep. of Germany

[73] Assignee: MED-Inventio AG, Zurich, Switzerland

[21] Appl. No.: 629,673

[22] Filed: Jul. 11, 1984

[30] Foreign Application Priority Data

Jul. 15, 1983 [DE] Fed. Rep. of Germany ....... 3325650

[51] Int. Cl.⁴ .............................................. A61B 17/00
[52] U.S. Cl. ................................. 128/303 R; 128/328; 604/95; 604/164
[58] Field of Search ............... 604/156, 95, 164, 170, 604/171; 623/12; 128/328, 303 R, 303 A, 348

[56] References Cited

U.S. PATENT DOCUMENTS

| | | | |
|---|---|---|---|
| 2,118,631 | 5/1938 | Wappler | 604/170 |
| 3,008,467 | 11/1961 | Morris | 128/328 |
| 3,137,298 | 6/1964 | Glassman | 128/328 |
| 3,349,526 | 10/1967 | Schuster . | |
| 3,452,740 | 7/1969 | Muller | 604/95 |
| 3,521,620 | 7/1970 | Cook | 604/170 |
| 3,547,103 | 12/1970 | Cook | 604/170 |
| 3,896,815 | 7/1975 | Fettel et al. | 128/348 |
| 3,922,378 | 11/1975 | Kline | 128/772 |
| 3,973,556 | 8/1976 | Fleischhacker | 128/772 |
| 4,215,703 | 8/1980 | Willson | 604/95 |
| 4,299,225 | 11/1981 | Glassman | 128/328 |
| 4,365,632 | 12/1982 | Kortam | 128/303 R |
| 4,456,017 | 6/1984 | Miles | 604/95 |
| 4,462,401 | 7/1984 | Burgio | 128/303 R |
| 4,473,073 | 9/1984 | Darnell | 128/303 A |
| 4,503,569 | 3/1985 | Dotter | 128/303 R |
| 4,529,400 | 7/1985 | Scholten | 604/95 |

FOREIGN PATENT DOCUMENTS

| | | |
|---|---|---|
| 1575701 | 1/1970 | Fed. Rep. of Germany . |
| 2428319 | 1/1976 | Fed. Rep. of Germany ...... 128/328 |
| 977515 | 4/1951 | France . |
| 0156901 | 11/1956 | Sweden .............................. 604/95 |

Primary Examiner—C. Fred Rosenbaum
Assistant Examiner—Gene B. Kartchner
Attorney, Agent, or Firm—Scully, Scott, Murphy & Presser

[57] ABSTRACT

A stiffening probe and tensioning device for use therewith. The probe comprises an elongated casing and a core longitudinally extending through the casing. This core includes front and back end portions respectively extending forward of and rearward of the casing, and respectively supported for longitudinal sliding movement relative to front and back ends of the casing. A stop element is connected to the front end portion of the core to limit rearward movement of that front end portion relative to the casing, and another stop element is connected to the back end portion of the core to facilitate pulling the core rearward relative to the casing. The tensioning device comprises a frame including front and back ends pieces, and front and back thrust pieces mounted on and longitudinally displaceable along the frame. A spring is held between the front end and front thrust pieces, and another spring is held between the back end and back thrust pieces. A bolt extends through the back end piece and threadably engages the back thrust piece to move the front and back thrust pieces along the frame. A holding device is connected to the front end piece to hold the casing of the stiffening probe, and another holding device is connected to the back thrust piece to hold the core of the stiffening probe.

25 Claims, 16 Drawing Figures

STIFFENING PROBE AND TENSIONING DEVICE THEREFOR

TECHNICAL FIELD OF INVENTION

The invention relates to a stiffening probe for medical use for therapeutic or diagnostic purposes, more particularly for insertion into the digestive or excretory tract. It also relates to a tensioning device for controlling the stiffening probe.

BRIEF DESCRIPTION OF PRIOR ART

There are various medical operations which can only be carried out with the aid of so-called stiffening wires. This is the case, for example, when tubes are placed in the duodenum for artificial feeding or the drawing off of fluid for diagnostic purposes. A pliable tube pushed perorally via the oesophagus into the stomach forms numerous coils when pushed further into the stomach, making it impossible to pass the tube out of the stomach into the duodenum. If a rigid wire is inserted into the tube the stomach can be passed through without any essential coil formation. Once the duodenum has been reached, the stiffening wire is removed from the tube.

Similar problems occur with the placing of oesophagus prostheses and prostheses in the region of the bileduct. However, these known stiffening wires have the disadvantage that they have a prescribed rigidity which acts disadvantageously when passing through organs where, for example, a more supple wire or, on the other hand, a more rigid wire would be more advantageous.

OBJECT OF THE INVENTION

The object of the invention is to provide a stiffening wire (stiffening probe), the rigidity of which can be continuously and controllably adjusted in a simple manner in accordance with requirements.

SUMMARY OF THE INVENTION

This object is achieved by a stiffening probe of a wire-like form formed by a Bowden wire consisting of a casing and a wire-core, the wire-core having at the insertion end a stop component which, when the wire-core is pulled at the end remote from the insertion end, comes to bear on the casing or attachment parts thereof.

The essential advantage of the invention consists in the fact that the rigidity of the probe can be increased as required and, what is more, by simple, small-scale means, namely by the principle known per se of the Bowden wire, utilizing the stiffening of the Bowden wire, which is produced by axial tension on the core and which in a standard Bowden wire is unimportant per se because, in a Bowden wire, what is important essentially is the transmission of longitudinally acting forces. According to the invention the insertion end of the core is supported on or held against the casing by a stop component. The tensile force is thus transmitted directly to the casing. As a result, this Bowden wire end is not supported as is usual in other Bowden wires, so that the insertion end is free for the appropriate operations. In order to produce the stiffening tension required for each case, a tensioning device is associated with the probe, which device engages the core by means of an adjustable member and in which the end of the casing nearer to it is held.

For a satisfactory operation a casing is required which is flexible transversely to its longitudinal direction and which cannot or can hardly be compressed in its longitudinal direction so that the desired stiffening can be achieved. This can be achieved by a flexible casing of specific initial rigidity. The faces of the sections lying adjacent one another may extend parallel to each other or also obliquely to each other. In the first case the probe tends to straighten itself when it stiffens. In the second case stiffened forms other than a straight form are possible for the probe, e.g. a curve. If the faces of the sections of the probe lying adjacent one another are spherical faces, the probe is able to stiffen in its respective form, which is important particularly when it is inserted into sensitive parts of the body. All the arrangements described above have the advantage for example that, for the insertion of a tube into the duodenum, the stiffening probe used as the insertion aid allows a relatively comfortable peroral insertion via the oesophagus into the stomach. When the front end of the tube enters the stomach, the stiffening probe can be made suitably rigid to enable the tube to be passed without problem into the duodenum. Once the duodenum has been reached, the stiffening probe is relaxed again and can be removed from the tube without any unpleasant effects on the patient.

The arrangements according to FIGS. 4-6 are advantageous for attaching or removing a tensioning device quickly and easily to the probe.

The stop component or components may, as required, take the form of a sphere of a disc arranged perpendicularly with its front face to the direction of pull, but they may also be of any other form advantageous for therapeutic or other purposes or for the rigid tensioning in the tensioning device.

The stop components can be fixed undetachably by gluing, welding or other method. However, they may also be removably attached by means of a screw thread for example. In the latter case, once the stop component has been removed, the core can be withdrawn from the casing and thus both parts can be more efficiently cleaned and sterilized. Also, a detachably fixed stop component can be replaced by a stop component of a different shape so that the stiffening probe can be adapted to the widest variety of medical applications.

It is advantageous if each end of the Bowden wire core projecting from the casing has a stop component or if there is a stop or fixing component at one end and an active component for therapeutic or diagnostic purposes at the other end.

The arrangement according to the shown embodiments enables solid specimens to be removed, for example a gall stone, or this arrangement may even be used for crushing a gall or bladder stone. The cage is formed in this case so that the core end pushed out from the casing allows the cage to expand radially to receive the stone. When the core is withdrawn, the cage will endeavor to press its longitudinally extending wires radially inwards and thus clamp the completely collapsed cage into the casing interior. By means of this radial inward pressure movement, a stone taken into the cage can be tightly held and removed from the body or even crushed such that the fine fragments of the stone can be secreted out of the organ.

Particularly when the casing is not a full-volume, one-piece body, but consists of coils or sections as shown in FIGS. 15 and 16, a relatively smooth surface can be achieved.

Contamination can be avoided by this means and the device kept clean more effectively. Also, a suitable plastics cover or other type of cover commonly used for medical purposes can be provided on all the outer surfaces of the probe according to the invention.

Furthermore, at the front end projecting from the casing, the probe according to the invention may have a flexible guide end projecting over the stop component to facilitate insertion of the probe.

Other shown arrangements also serve this same purpose, simultaneously allowing an easy and convenient connection of a tensioning device or an easy and convenient blocking of the movement of the core and casing.

The invention further contains design features which enable movement to be blocked between a probe and a propelling member to be slipped onto the probe. For this purpose a clamp component can be advantageously used, fixed either on the propelling member or on the probe, or a coupling component, which co-operates with a coupling component attached in each case to the other component. This arrangement considerably simplifies the manipulation of the probe during the insertion of a prosthesis or such like.

The tensioning device as embodied in FIGS. 7-10 is distinguished not only by a simple method of construction, but it also allows ease of operation when the probe is stiffened. When the probe needs to be stiffened, the end of the core having a stop component or fixing component is placed into the holding device of the second thrust piece and the casing of the Bowden wire pulled manually against the force of the small, flexible spring until the casing end can be inserted into the holding device provided on the first cross-piece. Following this, the threaded bolt is turned to move it from the second thrust piece towards the first thrust piece until the front end of the threaded bolt is adjacent to the front face of the first thrust piece under only slight tension. This enables the initial tension required for the insertion now to be reached which allows the probe to have sufficient flexibility. By further advancing the threaded bolt, the distance between the first cross-piece and the second thrust piece is increased against the force of the stronger spring and, by the simultaneous withdrawal of the core, the probe obtains its desired rigidity.

The design according to FIG. 6 is distinguished by its simplicity, combined with efficient operation. The guide rods serve simultaneously to receive and guide the pressure springs and, in addition, represent the longitudinal sides of the frame of the device.

Other embodiments of the invention hold the end of the casing remote from the insertion end, the slot allowing insertion of the casing and the socket allowing the casing to be received. This socket may be of conical shape, by means of which the casing end inserted into it is clamped there. However, it may also be a cylindrical bore which has a slightly greater diameter than the external diameter of the casing. The front face of the inserted casing bears on the base of the bore, while the casing face of the inserted end is simultaneously guided and radially supported in the cylindrical bore. This, in addition, avoids kinks in the Bowden wire. Another feature of the invention enables the tensioning device to be connected to probes having different diameters of differently sized casings or cores. It is advantageous in such a case for the first holding devices to be arranged in at least one carrier which is held moveably on the tensioning device to such an extent that the first holding devices can each be brought into a specific operating position. An advantageous embodiment for such a solution is, for example, a turret head.

The same advantages also apply to the other embodiments. The core is placed into the slot of the second holding device such that the stop component is against the front face of the second holding device opposite the first holding device. It is particularly advantageous if this second holding device is of a semi-circular design curving away from the first holding device thereby ensuring a secure fixing of the stop component, more particularly in its spherical form. In this connection this holding device can be formed of a sheet material which is curved into a C-shape with the slot in its curved portion. On the other hand, the embodiment of FIGS. 11-12 provides means for enabling different sizes or different shapes of probe to be inserted into several adjacent second holding devices, in which case the second holding devices have different shapes, e.g. slots of varying widths. On the other hand, within the scope of the design, it is possible to arrange one or more second holding devices displaceably so that they can be brought into a specific operating position. If several second holding devices are arranged in series in the longitudinal direction, it is possible for probes of different lengths to be received or for different positions of the core relative to the casing to be accommodated.

In order to enable the use of probes of different dimensions or shapes, it is also possible to mount the holding devices detachably so that when, for example, a thicker probe is used, a correspondingly sized holding device can be substituted. In this way, by providing a single device and by using several interchangeable holding devices, probes of different dimensions can also be tensioned, which substantially increases the economy of this device. A marking similar to that of a measuring tape may be advantageously applied in a known way on the inwardly pointing side of the upper surface of at least one of the side parts or of the frame. In addition, on the first thrust piece a transversely arranged marking line can be applied which, in conjunction with the above-mentioned marking, indicates the degree of tension of the stiffening probe.

Finally, another feature of the invention relates to the use of the tensioning device as a locking device for the probe. For this purpose an additional clamping device, such as, inter alia, a locking screw is provided on the second thrust piece, which clamping device clamps the second thrust piece on the guide elements. In this way the second thrust piece can be locked at a prescribed distance relative to the first cross-piece, by which means the length of the core parts projecting from the casing can be fixed.

BRIEF DESCRIPTION OF THE DRAWINGS

In the following, with reference to the drawings, the invention is described in more detail with reference to several exemplary embodiments of the stiffening probe and the tensioning device, in which.

DETAILED DESCRIPTION OF THE PREFERRED EMBODIMENT OF THE INVENTION

Figure 1:
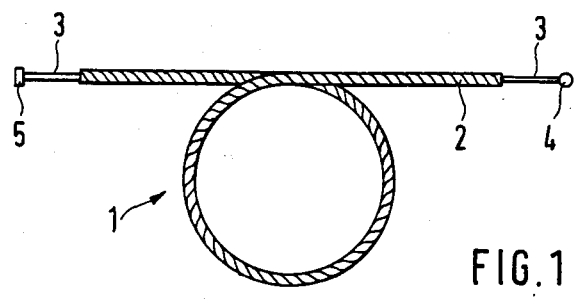
FIG. 1 shows a plan view of a stiffening probe according to the invention, having one spherical and one discoid stop component.

As can be seen from FIG. 1, the stiffening probe according to the invention consists of a spiral casing 2 and a flexible core 3 disposed therein so as to be axially displaceable. Stops are attached to each of the two ends of the core 3 projecting from the casing 2, the stops being in this embodiment, by way of example, one spherical stop component 4 and, at the other end, one discoid stop 5.

Figure 2:
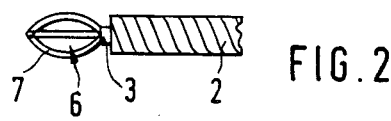
FIG. 2 shows one end of a stiffening probe according to the invention, having a cage-like stop component.

As can be seen from FIG. 2, the stop component may also be a cage 6 formed by longitudinally extending elastic spring steel wires 7.

Figure 3:
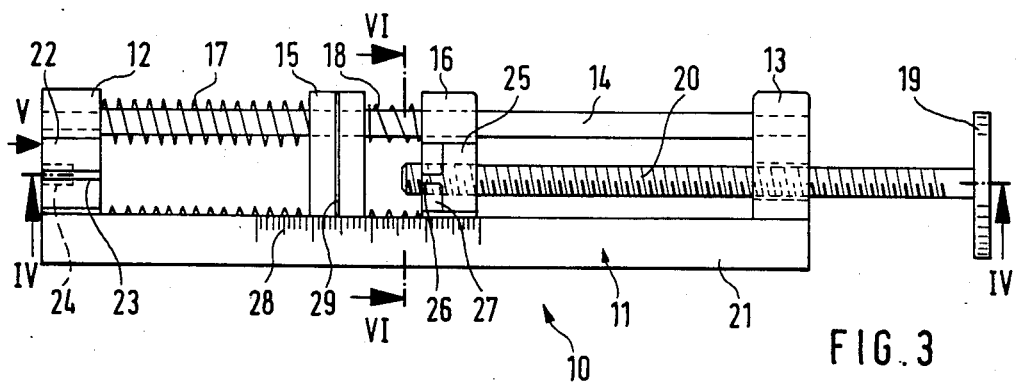
FIG. 3 shows a plan view of a tensioning device according to the invention, with one side part removed.
Figure 4:
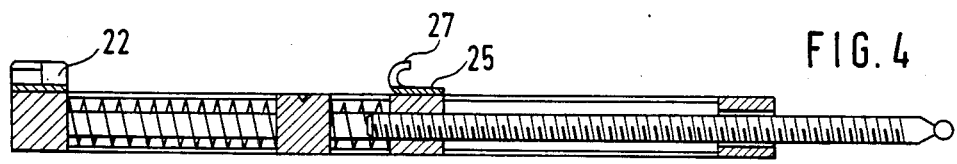
FIG. 4 shows an axial section along lines IV—IV from FIG. 3.
Figure 5:
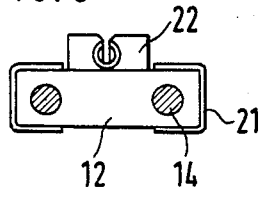
FIG. 5 shows a view according to arrow IV from FIG. 3.
Figure 6:
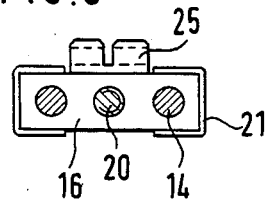
FIG. 6 shows a section according to lines VI—VI in FIG. 1.
Figure 7:
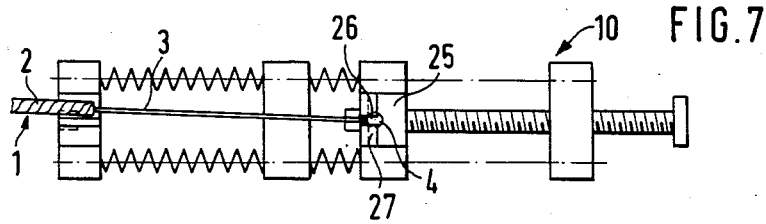
FIGS. 7-10 in each show plan view of the tensioning device according to the invention in different stages of operation.
Figure 8:
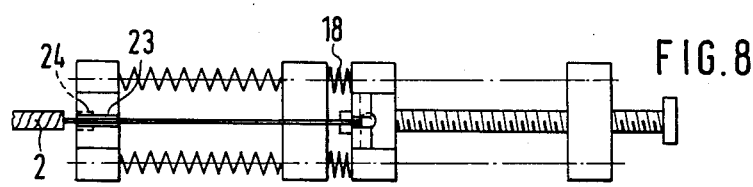
Figure 9:
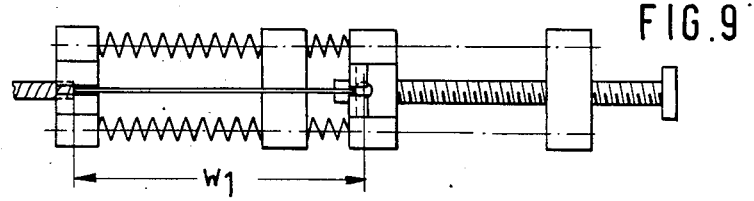

As shown by FIGS. 3 and 4, the tensioning device 10 has a first and second narrow cross-piece 12, 13 respectively which cross-pieces are fixedly joined together at their ends by means of guide rods 14 to form a rectangular frame 11.

Between the cross-pieces 12 and 13 first and second thrust pieces 15, 16 respectively are arranged slidingly or axially displaceably on the guide rods 14. A long, stiff pressure spring 17 is arranged between the cross-piece 12 and the first thrust piece 15 and a short soft spring 18 is arranged between the first thrust piece 15 and the second thrust piece 16, both springs being carried axially on the guide rods 14.

A threaded bolt 20 having a handle piece 19 is centrally arranged such that it penetrates the second cross-piece 13 through a smooth guide bore, while it is screwed into the second thrust piece 16 via a threaded bore.

U-shaped side pieces 21 are fixed detachably to the frame 11 at both longitudinal sides and contribute to the small and compact construction of the device. In the representation according to FIG. 3, one of the side pieces 21 has been omitted in order better to show the assembly of the device.

A first holding device 22 is fixed detachably by means of screws or the like on the first cross-piece 12. On the upper side of the holding device 22 an axial slot 23 is provided which, at its outwardly pointing side, has a cylindrical socket 24 in the form of a bore.

A second holding device 25 is fixed detachably by means of screws or the like on the upper side of the second thrust piece 16. This holding device also has a slot 26 which is open towards the top for the insertion of the core 3. The holding device 25 is of a hook-like form, its straight portion serving for attachment to the thrust piece and its curved hook portion 27 for the attachment of the stop component 4.

A marking 28 similar to that of a measuring tape is applied in a known manner on the upper side of one of the side pieces 21, while the first thrust piece 15 has a marking 29.

As can be seen from FIGS. 7 to 10, in order to tension the stiffening probe, one of its ends is inserted into the tensioning device 10. Namely, the projecting end of the core 3 is inserted into the holding device 25 so that the core is pushed through the slot 26 and the stop component 4 is securely caught in the hook portion 27 (see FIG. 7). Then, tension is exerted by hand in the longitudinal direction of the device until the casing part 2 releases a length of the core 3 which allows the core to be inserted into slot 23. In this connection the thrust piece 16 is displaced against the force of the spring 18 in the direction of the fixed thrust piece 15 which is not essentially moved by this slight tensile force. Once the core 3 has been successfully placed into the slot 23, the casing 2 is released so that it slips into the socket 24 under the force of the spring 18. In this way a state of only slight initial tension is achieved in the stiffening probe. The stiffening probe 1 has the desired flexibility for insertion, for example, via the oesophagus into the stomach.

Figure 10:
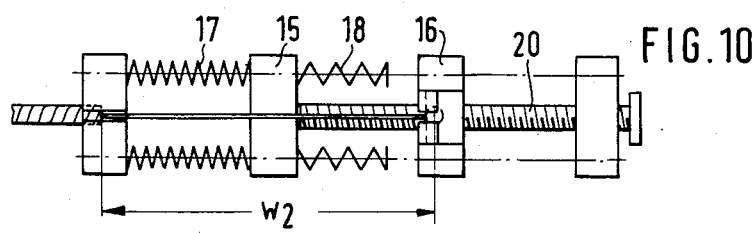

If, once it has reached the stomach, the stiffening probe needs to have greater rigidity, then, as can be seen from FIG. 10, the threaded bolt 20 is screwed with the aid of its handle part 19 into the threaded bore of the second thrust piece 16 until the front face of the threaded bolt 20 is against the front of the first thrust piece 15 facing it. The threaded bolt is then screwed in further in the same direction so that the distance between the two thrust pieces 15 and 16 is increased. As the spring 17 is a relatively rigid spring, the thrust piece 15 compresses this spring 17 only to a slight degree while, by increasing the distance between the two thrust pieces 15 and 16, the distance between the front face of the casing and the stop face of the stop component 4 is increased. The high tension force produced in this way between the core and casing produces a high degree of rigidity in the stiffening probe 1.

The Bowden wire used as the stiffening probe 1, in respect of the lengths of the casing and the core, and also the device, in respect of the effective distances $W_1$ and $W_2$, must have dimensions coordinated to each other. Also, the springs 17 and 18 must be matched in their spring range and spring characteristic to the required traction and tension forces.

The tensioning device according to the invention may also be constructed in another way which has not been shown, by an alternative arrangement of the springs and the thrust elements relative to each other.

A simpler, but not so optimally effective embodiment can be achieved by providing only the thrust piece 15 which is pressed directly against a pressure spring 17 via a threaded bolt screwed in the fixed cross-piece 13. In the compressed state the stiffening probe can be hooked into a holding device 25 provided on the upper side of the thrust piece 15 and inserted in the holding device 22. The Bowden wire can then be stiffened by unscrewing and thus releasing the tension of the screw 17.

Figure 11:
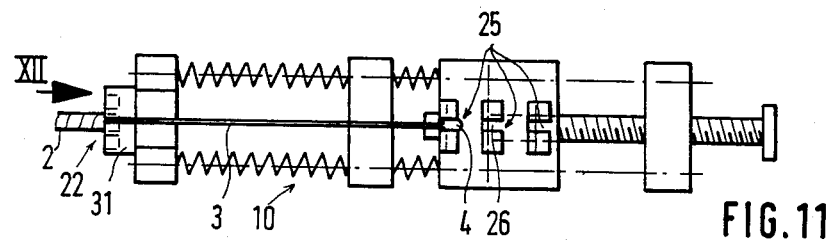
FIG. 11 shows a tensioning device constructed according to the invention, as a second exemplary embodiment.
Figure 12:
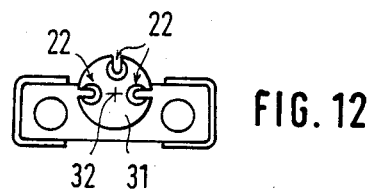
FIG. 12 shows a view onto the tensioning device according to FIG. 11 in the direction of arrow XII.

The second exemplary embodiment of the tensioning device 10 according to FIGS. 11 and 12 differs from the first exemplary embodiment merely in that three first holding devices 22 are provided which are constructed on one carrier 31 which is rotatable about an axis of rotation 32 so that in each case one of the first holding devices 22 can be brought into the desired operating position. The advantage of this arrangement consists in the fact that probes of different sizes or shapes can be connected to the tensioning device 10. Moreover, the first holding devices 22 are each designed so that they can receive the casing of the relevant probe.

Three second holding devices 25 are also provided for the end of the core 3 of the probe projecting from the casing 2. However, these three holding devices lie in series in the longitudinal direction of the tensioning device 10, which enables probes to be connected to the tensioning device 10 which have stop components 4 at varying distances from the casing 2. In FIG. 11 three curved sheet material angle pieces having slots 26 according to the first exemplary embodiment are arranged in series. A further advantageous embodiment for second holding devices 25 arranged in series can consist in providing a through slot with clearances (recesses) at specific intervals along the slot, to receive the stop components 4.

Figure 13:
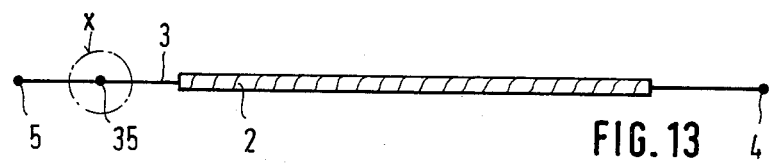
FIG. 13 shows a probe constructed according to the invention, as a third exemplary embodiment.
Figure 14:
FIG. 14 shows a detail of the third exemplary embodiment.

In the third exemplary embodiment according to FIGS. 13 and 14, the probe according to the first exemplary embodiment consists of a casing 2 formed by coils and a core 3 passed therein with a front stop component 5 and a rear stop component 4 of spherical form. Moreover, a further stop component 35 is arranged on the core 3 at a distance from the stop component 5. The purpose of the stop component 35 is as follows.

If, when the probe is being tensioned, the stop component at the front end of the core 3 becomes detached as a result of the tension force, for example because of a faulty solder joint, it will fly back with great force as a result of the pretension of the casing 2, which could in theory lead to injuries. In the third exemplary embodiment the stop component 35, which, during tensioning, comes to bear on the casing 2, is stressed during the tensioning instead of stop component 5. If the stop component 35 becomes detached unintentionally during tensioning, it is not lost but is held by the stop component 5. Also, the probe remains operational because the stiffening of the probe can be continued as a result of the presence of the stop component 5.

FIG. 14 shows the detail characterized by X in FIG. 13 in an enlarged, sectional representation. The stop component 35 is a sphere with a bore, which is slipped onto the core 3 and soldered.

It is also possible within the scope of the invention to provide several additional stop components 35.

The external diameter of a probe is limited on the one hand by the fact that the diameter of the core 3 must not substantially exceed approximately 1 to 1.5 mm, as otherwise it becomes too rigid, leading to difficulties when inserted into a stenosis. Also, particularly in the case of a casing 2 consisting of coils, the clearance between the inner wall of the casing 2 and the core 3 must only be slight as, otherwise, the casing 2 forms undulations when the probe is tensioned and, in the case of a casing 2 consisting of coils, individual coils are pushed over one another. Also, in an exemplary embodiment of this type, the wall thickness of the casing 2 cannot be freely increased as the casing 2 becomes too rigid if the coils have a thickness of more than 0.6 to 0.8 mm.

Figure 15:
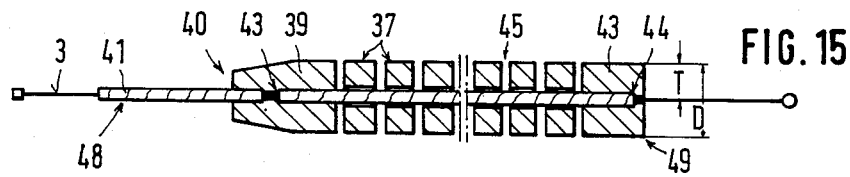
FIG. 15 shows a probe constructed according to the invention, as a fourth exemplary embodiment.
Figure 16:
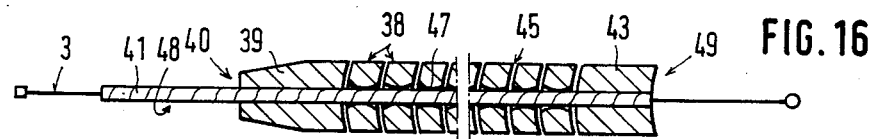
FIG. 16 shows a probe constructed according to the invention, as a fifth exemplary embodiment.

It is possible for the casing 2 to have a greater external diameter without increasing the rigidity of the unstiffened probe if the casing 2 consists of annular sections 37, 38 lying one behind the other in its longitudinal direction according to the fourth and fifth exemplary embodiment according to FIGS. 15 and 16 and which are held movably together. The sections 37, 38 can be held together in various ways, e.g. by an outer cover common to all the sections 37, 38 (flexible tube) which protects from dirt the sections 37, 38 and also the spaces therebetween. It is important that the core 3 is either in connection with the first section 39 or may be pulled with the stop component 5 directly or indirectly against the first section 39 in order to effect stiffening. The stiffening is produced by the tension which exists in the mutual contact of the sections 37 to 39. In this connection the sections 37 to 39 need not adjoin each other over the entire surface, as a stiffening is already produced with a point contact, in which case the probe can have a form other than a straight form.

In the exemplary embodiments to be described, the casing, designated generally by 40, of the probe is formed by a core casing 41 made of homogeneous material (for example plastics) or of adjacent coils and on which the annular sections 37, 38 are mounted and held together. The first section 39 and the last section 42 are rigidly attached to the core casing 41, for example by soldering. In order to increase stability, the first section 39 and the last section 42 engage in an interlocking manner on the inner section of the core casing 41 at the points designated by 43 and 44. At these points 43, 44 the core casing 41 is interrupted or shortened and the sections 39, 42 grip behind the front faces of the core casing 41 by means of projections. A portion of prescribed length of the core casing 41 projects from the section 39 on the insertion side to facilitate insertion. Likewise for the purpose of facilitating insertion, the first section 39 tapers conically in each case. In the fourth and fifth exemplary embodiment, not only is a greater probe diameter D available, but also a greater rigidity can be achieved because greater radii r are present, the magnitude of which determines the degree of stiffening.

The fifth exemplary embodiment according to FIG. 16 differs from the fourth according to FIG. 15 in that the faces 45 of the sections 37, 38 lying adjacent one another are spherical faces. This allows a stable stiffening even when the probe has a form other than a straight form, for example is simply curved or curved in an S shape. Also, in the fifth exemplary embodiment there are no stop edges, designated in FIG. 15 by 43 and 44. In the fifth exemplary embodiment, the first section 39 and the last section 42 are fixed by soldering on the metal casing 41 consisting of coils.

In order to increase flexibility, it is advantageous to provide a clearance in the bores 47 for the core casing 41. Flexibility is particularly improved if—as represented in FIG. 16—the bores 47 expand outwardly in each case.

To tension the probe according to FIGS. 15 and 16, the end 49 of the casing 40 remote from the insertion end 48 is received in the first holding device 22 of a tensioning device 10. It has proved advantageous here to provide first holders 22 of various sizes on the tensioning device 10.

Figure 17:
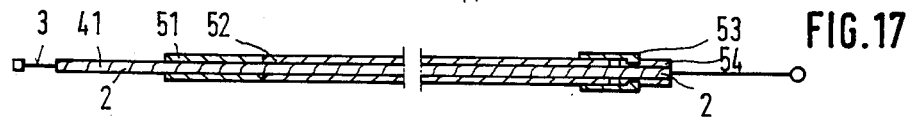

The sixth exemplary embodiment according to FIG. 17 shows a probe constructed according to the invention, prepared for the insertion of a bileduct prosthesis 51 in the form of a plastics tube. The prosthesis 51 is slipped on the casing 2 at the insertion end of the probe. Behind the prosthesis 51 there is a propelling member 52 in the form of a flexible tube, which serves to push the prosthesis 51 onto the required position when the probe is in the inserted position.

Attached at the rear end of the propelling member 52 is a first coupling member 53 which is coupled to a second coupling member 54 fixed on the casing 2. In a preferred embodiment, the coupling members 53, 54 are Luerlock-connectors known in the medical field and emminently suitable for this purpose.

The purpose of the coupling members 53, 54 is to produce a connection between the probe (casing 2) and the propelling member 52 so as to preclude relative displacement between these components.

When a probe is inserted relative displacement can occur if the insertion end meets resistance during insertion, which attempts to displace the probe and the propelling member 52 outwards. Also, the stiffening of the probe leads to a force component which then brings a laterally acting force to bear on the probe when it is stiffened in an inserted position in a curved place. The doctor performing the operation is considerably hampered even by the tendency of a relative displacement. The operation may even fail if relative displacement occurs because the prosthesis 51 assumes an unsuitable position.

To prepare the probe, the propelling member 52 is firstly slipped on from the insertion end and secured on the probe with the aid of the coupling members 53, 54. Then the prosthesis 51 is slipped on from the insertion end. In order to be able to adjust the position of the prosthesis 51 on the probe, it is advantageous for the coupling member 54 to be arranged adjustably on the probe and so it may be fixed in the required position in each case, in the present instance, on the casing 2. A locking screw for example may serve this purpose.

The securing of the propelling member 52 with the aid of the coupling consisting of the coupling members 53, 54, according to the invention, is also advantageous with known probes of the type which cannot be stiffened according to the invention and which consist, for example, only of one core 3. When probes of this type, too, are inserted, force components are acting—as already mentioned—which attempt to move the probe outwards. Thus, the design according to the invention also represents a considerable aid to doctors operating with such probes.

The measure entailing the insertion of a prosthesis 51 and propelling member 52 onto an inserted probe from the rear end is disadvantageous. For one thing, because with a propelling member 52 of approximately 1.5 m in length, difficult manipulation is required, for another because the position of the inserted probe can only be controlled if it is always projecting at its rear end from the propelling member 52, i.e. is approximately 1.5 m longer than would otherwise be necessary. Such a long probe is unwieldy.

What is claimed is:

1. A tensioning device for use with a stiffening probe including an elongated casing and a core longitudinally extending therethrough, the tensioning device comprising:
   a frame including front and back end pieces, and at least a first longitudinally extending guide member connecting together said end pieces;
   front and back thrust pieces mounted on and longitudinally displaceable along the guide member;
   a first spring held between the front end piece and the front thrust piece;
   a second spring held between the front and back thrust pieces;
   a threaded bolt extending through the back end piece and the back thrust piece, and threadably engaging the back thrust piece to move the front and back thrust pieces along the guide member, the threaded bolt including a handle to facilitate turning said threaded bolt;
   front holding means connected to the front end piece to engage and hold a back end of the casing of the stiffening probe; and
   back holding means connected to the back thrust piece to engage and hold a back end of the core of the stiffening probe.

2. A tensioning device according to claim 1 wherein:
   the frame further includes a second guide rod longitudinally extending parallel to the first guide rod, and further connecting together the front and back end pieces;
   each of the front and back thrust pieces includes first and second bores;
   the first guide member longitudinally extends through the first bores of the front and back thrust pieces; and
   the second guide member longitudinally extends through the second bores of the front and back thrust pieces.

3. A tensioning device according to claim 1 wherein the front holding means includes a longitudinally extending slot to receive the core of the stiffening probe, said slot including a forward socket to receive and hold the back end of the casing of the stiffening probe.

4. A tensioning device according to claim 3 wherein the socket has a conical shape.

5. A tensioning device according to claim 3 for use with a stiffening probe having a casing with a preset diameter, and wherein the socket has a cylindrical shape coaxial with the slot, and with a diameter slightly greater than said preset diameter.

6. A tensioning device according to claim 1 wherein the front holding means include a plurality of holding devices, each holding device including a slot to receive the core of the stiffening probe.

7. A tensioning device according to claim 1 wherein the back holding means includes an upwardly open slot to receive the core of the stiffening probe.

8. A tensioning device according to claim 1 wherein the back holding means includes a hook having a forward curved portion forming a slot to receive the core of the stiffening probe.

9. A tensioning device according to claim 1 wherein the back holding means comprises a plurality of longitudinally spaced apart holding devices.

10. A tensioning device according to claim 1 wherein the back holding means comprises a plurality of transversely spaced apart holding devices.

11. A tensioning device according to claim 1 wherein the frame further includes first and second U-shaped side coverings releaseably connected to the front and back end pieces.

12. A tensioning device according to claim 1 wherein the frame includes markings to facilitate judging the position of the front and back thrust pieces.

13. A tensioning device according to claim 12 wherein the front thrust piece also includes markings to help determine the position of the front thrust piece.

14. A tensioning device according to claim 1 for use with a stiffening probe adapted to be connected to the tensioning probe by hand.

15. A tensioning device according to claim 1 wherein the back thrust piece includes means releasably locking the back thrust piece in a fixed position on the guide member.

16. A stiffening probe comprising: an elongated, flexible casing adjustable between relaxed and stiffened states, and forming a longitudinally extending inside passage; the casing comprising a multitude of sections longitudinally lying adjacent to each other, each section including longitudinally opposite first and second faces, the first face of each section being convex and the second face of each section being concave, and the first face of each section being adjacent the second face of another section;
- an elongated core extending through the inside passage, and including
  - (i) a front end portion extending outside the casing, forward of and supported for longitudinal sliding movement relative to a front end of the casing, and
  - (ii) a back end portion extending outside the casing, rearward of and supported for longitudinal sliding movement relative to a back end of the casing;
- a first, front stop element connected to the forward end portion of the core, outside the casing, to limit rearward movement of the front end portion of the core relative to the casing; and
- a second, back stop element connected to the back end portion of the core, outside the casing, to facilitate pulling the core rearward relative to the casing to pull the casing from the relaxed state to the stiffened state.

17. A probe according to claim 16 wherein the sections of the casing are supported for movement relative to each other on the core.

18. A probe according to claim 16 wherein the front stop element comprises a spherical or discoid component.

19. A probe according to claim 16 wherein the front stop element is releaseably connected to the core.

20. A probe according to claim 16 further comprising screw means releaseably connecting the front stop element to the core.

21. A probe according to claim 16 wherein the front stop element comprises a cage including a plurality of longitudinally extending resilient steel wires.

22. A probe according to claim 16 wherein the casing includes an outer surface, and at least said outer surface has a substantially smooth plastics coating.

23. A probe according to claim 16 further comprising:
- a prosthesis movably mounted on a forward end portion of the casing;
- a tubular, propelling member mounted on the casing, rearward of the prosthesis; and
- means releasably holding the propelling member to the casing for unitary longitudinal movement therewith.

24. A stiffening probe according to claim 16, further comprising
- a third stop element connected to the forward end portion of the core, forward of the first, front stop element, to help keep the first, front stop element on the core.

25. A stiffening probe according to claim 24 further comprising means releaseably connecting the first front stop element to the core.

* * * * *